United States Patent [19]
Guirguis

[11] Patent Number: 5,003,988
[45] Date of Patent: Apr. 2, 1991

[54] MODULAR MULTIPLE FLUID SAMPLE PREPARATION ASSEMBLY

[75] Inventor: Raouf A. Guirguis, Rockville, Md.

[73] Assignee: La Mina Ltd., British Virgin Isls.

[21] Appl. No.: 396,655

[22] Filed: Aug. 22, 1989

Related U.S. Application Data

[63] Continuation-in-part of Ser. No. 369,610, Jun. 21, 1989.

[51] Int. Cl.$^5$ .............................................. A61B 5/00
[52] U.S. Cl. ..................................... 128/771; 604/404
[58] Field of Search ..................... 128/760, 761, 771; 604/317, 318, 403, 404; 422/102

[56] References Cited

U.S. PATENT DOCUMENTS

| | | | |
|---|---|---|---|
| 3,312,221 | 4/1967 | Overment | 604/317 |
| 3,777,739 | 12/1973 | Raitto | 128/2 |
| 3,881,465 | 5/1975 | Raitto | 128/2 |
| 4,040,791 | 8/1977 | Kuntz | 23/259 |
| 4,042,337 | 8/1977 | Griffith | 23/259 |
| 4,084,937 | 4/1978 | Beach | 23/259 |
| 4,244,920 | 1/1981 | Manschot et al. | 422/102 |
| 4,473,530 | 9/1984 | Villa-Real | 128/762 |
| 4,492,258 | 1/1985 | Lichtenstein et al. | 128/761 |
| 4,557,274 | 12/1985 | Cawood | 128/760 |
| 4,573,983 | 3/1986 | Annis | 604/322 |
| 4,661,100 | 4/1987 | Rechsteiner | 604/317 |
| 4,685,472 | 8/1987 | Muto | 128/760 |
| 4,700,714 | 10/1987 | Fuisz | 128/767 |
| 4,741,346 | 5/1988 | Wong et al. | 128/760 |

Primary Examiner—Max Hindenburg
Attorney, Agent, or Firm—Gipple & Hale

[57] ABSTRACT

An apparatus for collecting and testing multiple biological markers comprising a tubular compartmentalized container holding covalently bound antigen beads and correlating anti-antibody beads contained in separated compartments. The biological fluid, namely urine, is collected in the tubular container and is forced to flow through the separated compartment of the compartmentalized container so that predetermined ligands become attached to the bead ligands to obtain a plurality of biological markers.

20 Claims, 4 Drawing Sheets

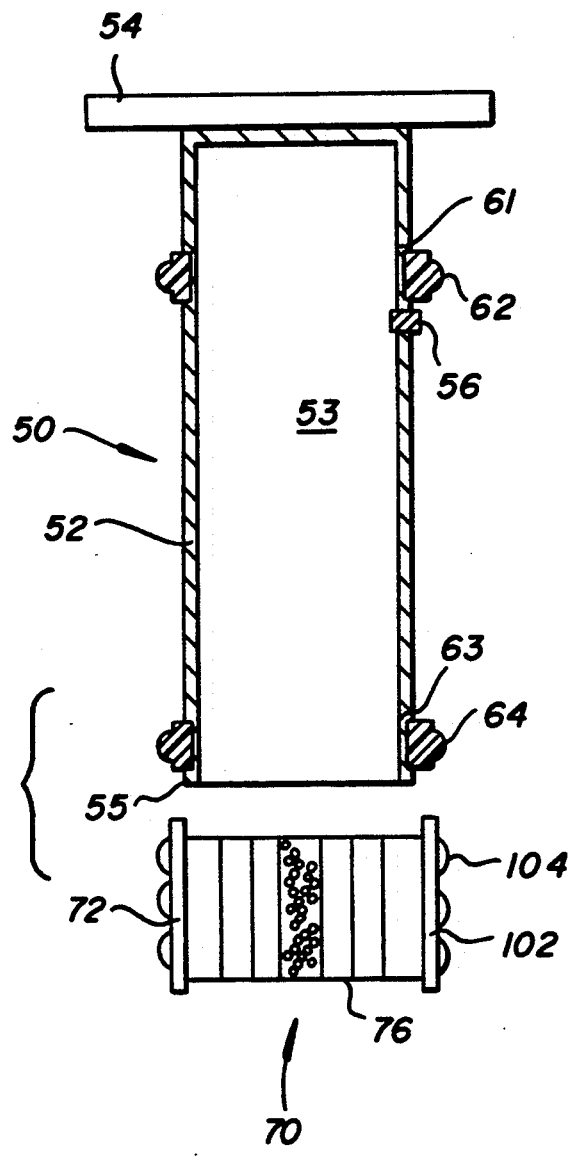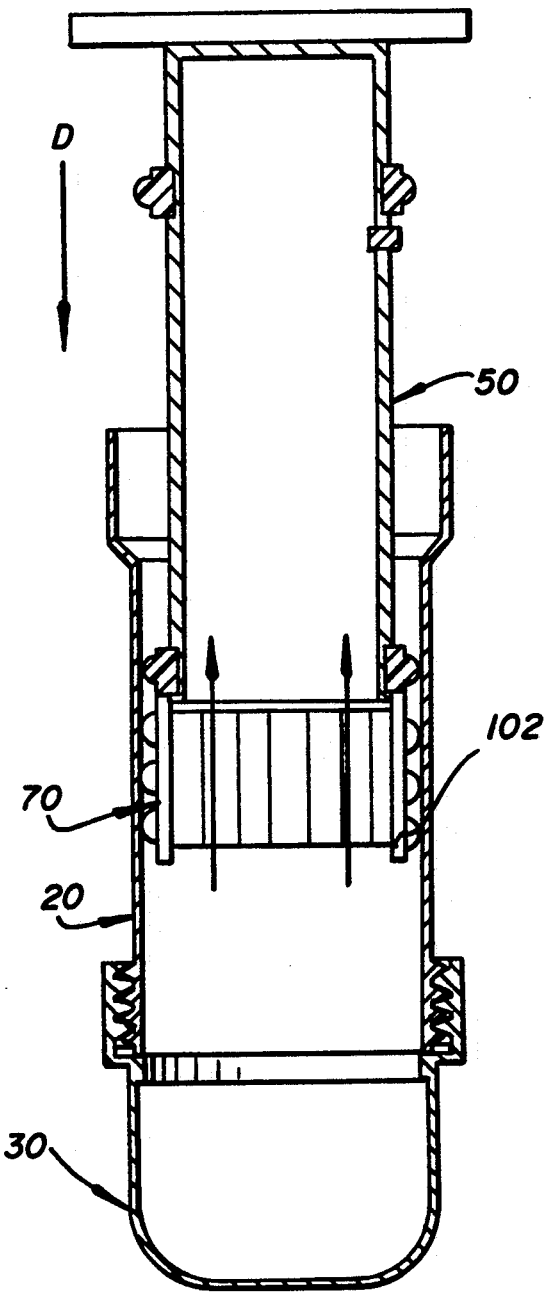
FIG. 3
FIG. 4

| ANTIGEN STATUS | AB″ | BA″ | AB | NONE |
|---|---|---|---|---|
| A+/B+ | − | + | + | + |
| A−/B− | + | + | − | − |
| A+/B− | + | − | + | + |
| A−/B+ | − | + | + | + |

MODULAR MULTIPLE FLUID SAMPLE PREPARATION ASSEMBLY

RELATED CASES

This application is a continuation-in-part application of U.S. patent application Ser. No. 07/369,610 filed June 21, 1989.

BACKGROUND OF THE INVENTION

The present invention is directed to medical and laboratory specimen collecting and testing equipment, and more specifically to an apparatus for detecting the presence of a plurality of specific antigens in biological fluids.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. In addition there is also the potential for specimen damage during the collection and/or shipment process as well as the potential for destruction of certain components of the specimen because the packaging does not screen particulants in the fluids or collects and holds different fluid components which will negate the test results or result in false data being obtained when the specimen is tested.

It has been noted that one of the problems in collecting biological fluid specimens occurs not only during the collection of the specimens but also in the transport or shipment of the specimens after collection to the laboratory for analysis.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

One such specimen collection device shown by U.S. Pat. No. 4,040,791 discloses a collection receptacle having a nipple upon which is mounted a specimen container which receives a predetermined amount of the specimen in a sealed condition. The specimen container is provided with an integally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle apparatus which uses a fluid sample such as urine and separates various antibodies from urine so that testing can be performed quickly and accurately with minimum time.

It is thus an object of the invention, particularly where antigens are being removed from the body fluids for a variety of tests to detect and visually indicate specific antigens in the body fluid samples. Previously such testing has been accomplished by a series of tests involving a number of different containers and expensive laboratory equipment. Mass testing using such a series of tests is expensive, time consuming, and often unsatisfactory.

BRIEF SUMMARY OF THE INVENTION

The invention is directed toward a multiple antigen marker analysis device. This device is in the form of a modular sample container in the housing, which can be washed or treated with biological fluids allowing the fluid sample to be quickly analyzed. The antibodies (against the antigen) and antigens are covalently bound to beads contained in concentric separated compartments formed in a single container. The antibodies can be provided prelabelled with coloring reagents. The testing sample is added to the container where the respective antigen reacts with the respective antibody to form antigen-antibody complex. If there is an absence of the antigen and/or antibody in the specimen sample the antibody will remain unoccupied. The beads housing unit contains three different sets of beads, one set with antigen covalently(irreversible) bound, one set with antibody covalently bound and the other set without antigen or antibody to act as a control.

In the accompanying drawings, there is shown an illustrative embodiment of the invention from which these and other of objectives, novel features and advantages will be readily apparent.

BRIEF DESCRIPTION OF THE DRAWINGS

FIG. 3 is an exploded cross sectional view of the piston assembly and sample/test container of the shuttle apparatus which fits into the sample collection apparatus of FIG. 1;

FIG. 4 is a cross sectional view of a sample filtration purification shuttle apparatus with direction of movement of the plunger shown by arrow D' and direction of flow of the fluid shown by arrows A;

DETAILED DESCRIPTION OF THE INVENTION

Figure 1:
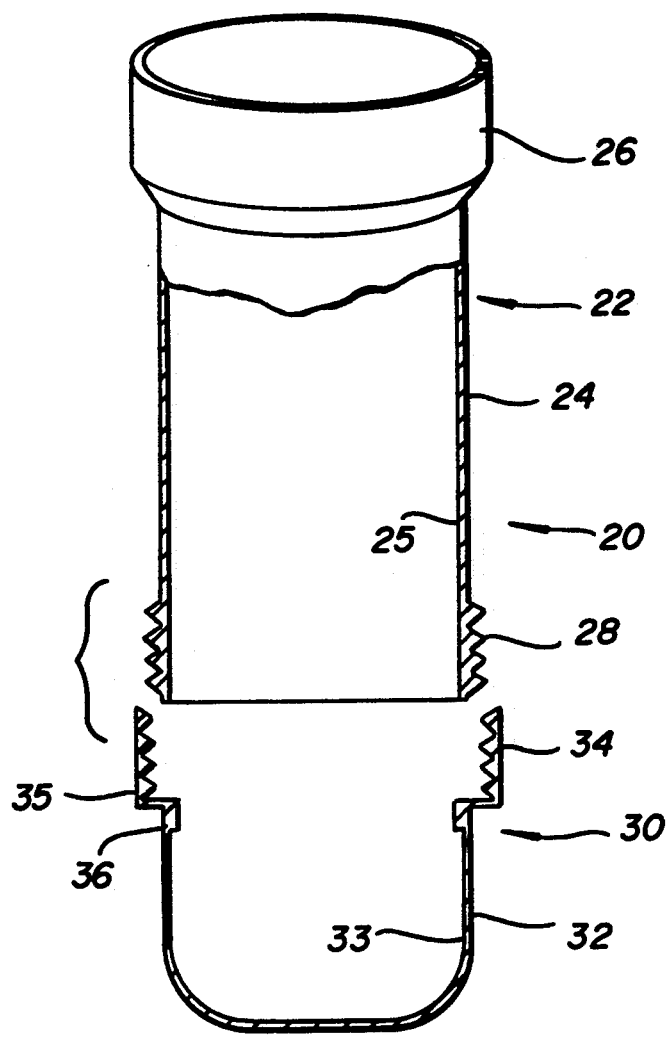
FIG. 1 is a cross sectional view of separated units of the sample collection apparatus of the invention.

The preferred embodiment and best mode of the invention is seen in FIGS. 1 through 6. The invention shown in the drawings comprises a modular fluid sample container with sample collection apparatus. While the invention can be used for any body fluid such as sputum, blood, body fluids or urine, it is primarily designed for use in collecting urine/blood samples for use in testing for the presence of various kinds of cancer in the body.

Figure 2:
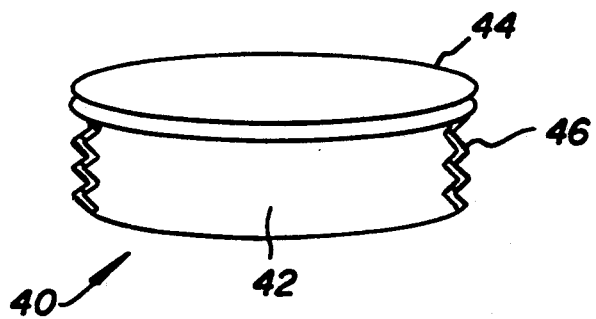
FIG. 2 is a cross sectional view of a cap for the shuttle storage unit of the sample collection apparatus of FIG. 1.

As shown in FIGS. 1 and 3 a sample collection apparatus 20 is constructed of polystyrene and comprises a tubular collection unit 22, a shuttle storage unit 30 and an associated cap member 40. The tubular collection unit 22 is constructed with a tubular open ended cylindrical body 24 having formed on one end an open flared end portion 26 and on the other end a threaded portion 28. The flared end portion 26 has a wide mouth to more easily receive body fluid which is loaded into the unit and also prevents entrapment of air between the bead container unit 70 and the surface of the sample fluid. The shuttle storage unit 30 is removably secured to the threaded portion 28. The shuttle storage unit 30 comprises a cylindrical cup shaped body 32 with a stepped female threaded open end 34 and shoulder 35. The open end 34 has a greater diameter than the diameter of body 32. A stop member 36 comprised of a circular ring or integrally formed rib is formed or secured to the inner surface of the shuttle body 32 immediately below the shoulder 35 of the threaded stepped open end 34. This stop member 36 serves as a stop for a transporter or shuttle assembly 50 shown in FIG. 3 which will be discussed later on in the specification. The cap member 40 as shown in FIG. 2 is formed with a cylindrical body 42 having a lid or cover 44 and external threads 46 which mate with the female threaded end portion 34 of the shuttle body 32. Thus the shuttle storage unit 30 and cap 40 can be used to form a closed container holding the particulants, testing material or fluid as desired. It should also be noted that a threaded or snug fitting cap (not shown) can be placed over end portion 26 so that the sample collection apparatus can be closed.

The transporter assembly 50 as shown in FIG. 3 is designed to fit within cylindrical body 24 and slideably move along the interior wall surface 25 in a sealed relationship and abut a shuttle sample container 70 for deposit within the shuttle storage body 32. The transporter assembly 50 is constructed of a transparent plastic comprising a hollow cylindrical piston body 52 provided with a thumb cover 54 and a bottom end member 55. An air release aperture 56 is formed in the piston body so that there is communication between the interior chamber 53 of the piston body into the outside atmosphere. The bottom end member 55 is porous and allows fluid flow therethrough into the interior chamber 53 as the exterior rigid surface engages the outer surface of the container 70. Mounted around the piston body in annular channels 61 and 63 cut into the exterior surface of the body 52 are respectively an upper O-ring 62 and lower O-ring 64. These O-rings slideably engage and form a fluid seal against the interior surface 25 of sample collection unit 22. The shuttle sample container 70 is adapted to receive end member 55 within the upper inner wall surface of the container cylindrical body 72 and has a diameter or size sufficient to allow it to be seated within the interior 33 of shuttle storage unit 30.

Figure 5:
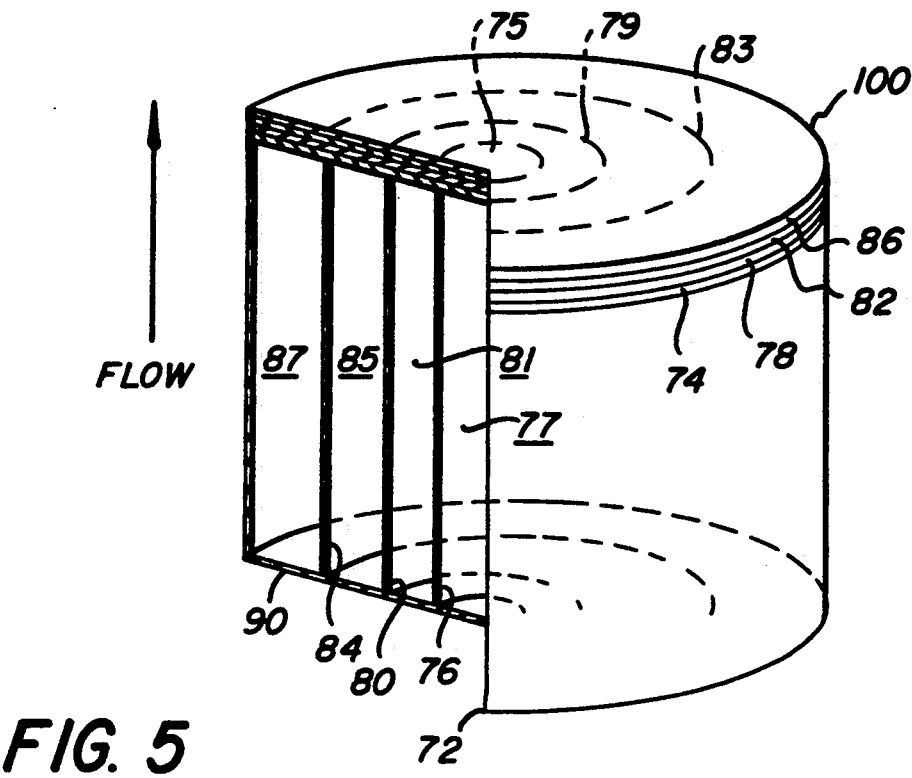
FIG. 5 is an enlarged perspective view partially in cross section of the sample test container.
Figure 6:
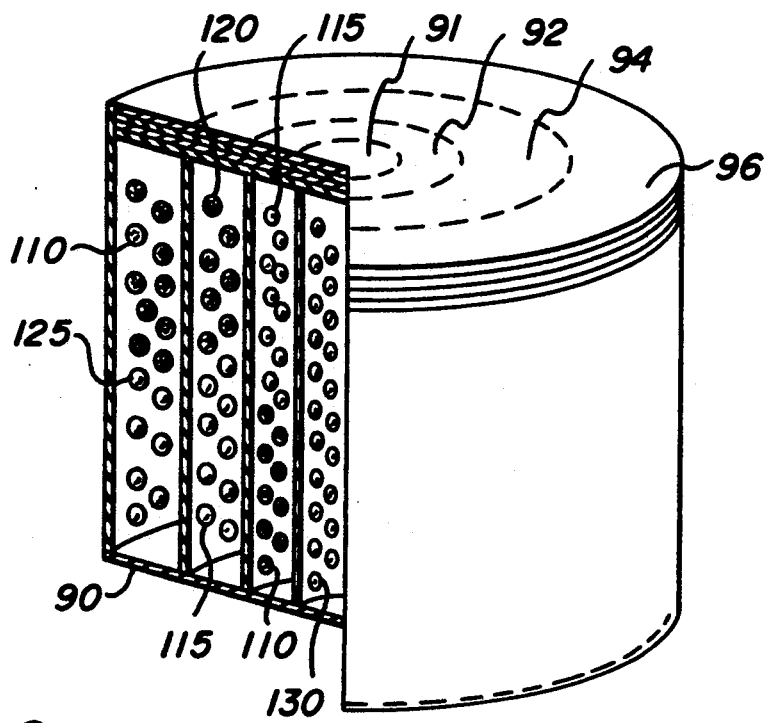
FIG. 6 is a view of the sample test container of FIG. 5 with labelled antigen and antibody beads positioned in the respective compartments.

The shuttle sample container 70 as clearly shown in FIG. 5 is constructed with a cylindrical body 72 open at both ends and threaded to allow the mounting of a porous circular center top member 74 which is threaded on the inside of the cylindrical body 72 and defines an aperture 83 which holds the outer cylinder 84. The outer cylinder 84 and associated top cover 74 are preferably sonically welded to each other but may be joined together by adhesive or any means known in the art.

Figures 7, 8:
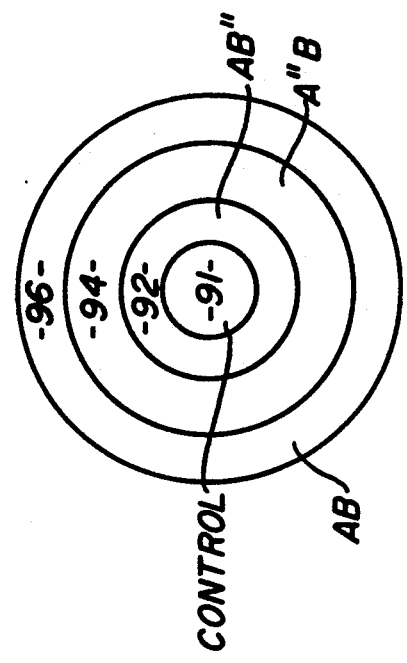
FIG. 7 is a table showing representation of the interpretation of test results.
FIG. 8 is a top plan view of the top surface of the sample test container showing different test zones.

A second top cover member 78 is stacked on top of the initial top member 74 and defines an aperture 79 which holds the first inner cylinder 80. A third top cover member 82 is stacked on top of the second top cover member 78 and defines an aperture 75 which holds a central cylinder 76. A top cover 86 is stacked on top of the third top cover member 82 to cover the top of the cylinder body 72. These porous cover members are secured to their respective cylinders as previously noted above and can be threaded on the inside of the cylindrical body 72 or constructed with a male/female mating construction on their upper and lower surfaces such as a tongue and groove which will allow the covers to be snapped together Alternately an outer cover (not shown) could be threadably mounted to the outside of the cylinder body 72 to hold the stacked cover members in fixed relationship to each other. The concentric nature and spacing of the respective cylinders 76, 80, 84 and 72 forms chambers 77, 81, 85 and 87. A circular disc membrane 100 preferably between 0.45-5.0 microns in thickness is positioned on the outer surface of top cover 86. A circular porous bottom cover 90 is threaded on the inside of the other end of cylinder body 72. The ends of cylinders 76, 80 and 84 abut against the upper surface of the bottom cover 90. Alternately the bottom cover 90 can be cut with circular grooves into which the ends of the cylinders 76, 80 and 84 fit or be provided with circular ribs into which the ends of the cylinders are seated and sealed. The body 72 cylinders 76, 80 and 84, top cover 86 and bottom cover 90 define a plurality of spaced chambers 77, 81, 85 and 87 which are filled with a predetermined sequence of beads which are covalently bound to various antigen and antibodies which constitute the biological markers. Positioned inside the central cylinder 77 is a test bead module 91 filled with unbound beads which acts as a control. The adjacent bead module 92 is filled with two sets of beads namely; antigen A, covalently bound beads 110 and anti-B antibody covalently bound beads 115. The adjacent outer bead module 94 is filled with two sets of beads namely; anti-B antibody covalently bound beads 115 and anti-A antibody covalently bound beads 120. The outer bead module 96 is filled with antigen B covalently bound beads 125 and antigen A covalently bound beads 110. Thus it can be seen that the beads are specifically combined to obtain a multiple marker test as shown in FIG. 8.

An O-ring sleeve 102 comprising a plurality of O-rings 104 is mounted to the exterior surface of the cylinder 72 formed by the sides of both top and lower covers 86, 90 when the same are fully screwed onto the body of the container 72. While specific sample beads have been described it is within the present invention that the chambers of the container 70 may be filled with sample beads of all forms and sizes which can be specifically manufactured for high affinity chromatography.

The beads can also have high affinity chromatography. The chemical and mechanical stability of the support (resin) and its linkage to the ligand (antigen) play a key role in affinity chromatography. Preferably as has been previously described the module bead chambers hold high affinity resin beads with specific antibodies or antigens immobilized onto the solid phase resin (e.g. Actigel-ALD, Protein A, Protein G . . . etc.) so that antigens in the sample can bind to their specific antibodies, or alternately the antibody complexes can become bound while passing through the resin module and become immobilized as well. The principle of affinity chromatography requires that a successful separation of a biospecific ligand is available and that it can be chemically immobilized to a chromatographic bed material, the matrix. Numbers of methods well known in the art have been used to couple or immobilize the antigen to a variety of activated resins. Examples of immobilization techniques which exhibit variable linkage are those formed by the reaction of the reactive groups on the support with amino, thiol, hydroxyl, and carboxyl groups on the protein ligand. The immobilized ligand must also retain its specific binding affinity for the substance of interest with the bound substances being selectively desorbed in an active form. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.)

In the case of Actigel-ALD a monomonic, stable, low reactively aldehyde group is introcuded to the support through 5 atoms hydrophilic spacer arm. This establishes well defined, stable secondary amine linkages without side reaction or the release of hydrophobic or reactive leaving groups. Another advantage to the use of Actigel-ALD is that it does not cross link proteins therfore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the device (approx 10-100 cm/min).

Visual affinity chromatography can be obtained through the use of color markers in the form of dye affinity chromatography product are available and are manufactured by TosoHaas under the designation TSK-GEL TOYOPEARL DYE AFFINITY CHROMATOGRAPHY PRODUCTS made with TOYOPEARL HW-65 as the base matrix and Cibacron Blue F3GA or reactive red 120 as the dye reagent. Blue-TOYOPEARL 650 and Red-TOYOPEARL 650 have differing protein binding capacities.

The shuttle resin/sample container 70 is pushed down until it enters into the body cavity 33 at which time the lower O-ring 64 engages stop rib 36 thus seating the shuttle resin/sample container 70 in a predetermined position so that it cannot break or damage the shuttle storage unit 30. When the shuttle resin/sample container 70 is seated in the shuttle storage unit 30, the upper "O" ring 62 becomes engaged with the inner surface 25 of cylindrical body 24. This will discontinue the communication between the body cavity 53 and the atmosphere through the air release aperture 56. Consequently the fluid entering the body cavity 53 will be trapped inside it even after removal of the shuttle storage unit 30 together with the seated resin/sample container 70.

The resin bead material with matrix and primary ligand (in this case antigen and antibody) having had flow contact with the fluid, namely urine, captures through antigen-antibody reaction or immune reaction the specific component of the fluid which is to be tested; and shows the multiple antigen marker status as per FIGS. 7 and 8. The primary antibodies against the antigens can be provided with prelabelled coloring reagents. A buffering reagent is also provided with the sample container to optimize the antigen antibody reaction (e.g. pH 8) since the urine pH is usually acidic. The testing sample is added to the container where the antigen reacts with the antibody to form antigen-antibody complexes. If there is an absence of the antigen in the specimen sample the antibody will remain unoccupied and will react with the antigen immobilized on beads. On the other hand, if the antigen is present, anitgen-antibody complexes will be formed. The beads housing container unit contains five different sets of beads having the ligand covalently bound thereto, one set with antigen A, and one set antigen B, one set with anti-A antibody and one set with anti-B antibody and the fifth set without any legand to act as a control. On the top of the beads housing, there is a circular (disk) high affinity membrane with immobilized secondary antibody against the primary antibody species. The upper surface of the disk membrane 100 provides the surface upon which the primary antibody and/or antigen-antibody complexes are captured by the secondary antibody immobilized on the top surface of the membrane and the test result is visualized.

The shuttle storage unit 30 is unscrewed from the tubular collection unit 22 with the shuttle resin/sample container 70 contained therein, the transporter assembly 50 remaining with the tubular collection unit 22 and cap 40 is screwed on threaded end 34 to keep the sample in a secured contained condition after adding the proper preservatives for analysis of the particulate matter or for testing by pouring color developing solution to visualize the prelabeled antibody captured on the top surface of the circular disk with the immobilized capturing secondary antibody.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An apparatus for collecting molecular samples from biological fluids to obtain multiple markers comprising a first container means; a sample collection storage unit removably mounted to said first container means, said sample collection storage unit comprising a container divided into plurality of bead containing compartments, control bead means positioned in one said compartments, at least two different antigen bead means located in at least another of said compartments; and at least two different anti-antibody bead means corresponding to said antigen bead means located in at least one other of said compartments.

2. An apparatus as claimed in claim 1 wherein said antigen bead means comprise beads having antigen A covalently bound thereto and beads having antigen B covalently bound thereto.

3. An apparatus as claimed in claim 1 wherein said anti-antibody bead means are anti-A antibody beads and anti-B antibody beads.

4. An apparatus as claimed in claim 1 wherein said plurality of compartments comprise at least 3 compartments; one of said compartment containing antigen A beads and anti-B antibody beads, another of said compartments containing anti-A antibody beads and anti-B antibody beads, and one compartment containing anti-B antibody and antigen B beads.

5. An apparatus as claimed in claim 1 wherein said plurality of compartments comprise at least 4 compartments; one of said compartments containing antigen A beads and anti-B antibody beads, another of said compartments containing anti-A antibody beads and anti-B antibody beads, another compartment containing anti-B antibody and antigen B beads, and yet another compartment containing antigen A beads and antigen B beads.

6. An apparatus as claimed in claim 1 wherein said container means comprises an outer body, a plurality of concentric tubular cases and a top cover means and a bottom cover means.

7. An apparatus as claimed in claim 1 wherein said container means comprises a cylindrical housing, cover plate means covering each end of said cylindrical housing, each cover plate means allowing flow of fluids therethrough, and membrane means extending across one end of the cylindrical housing, said membrane means being provided with immobilized secondary antibody against the primary antibody species.

8. An apparatus as claimed in claim 7 wherein said membrane means comprises a membrane ranging from 0.45 to 5.0 microns in thickness.

9. An apparatus for collecting multiple markers from biological fluids comprising a tubular container; a specimen collection unit mounted in said tubular container, said specimen collection unit comprising a housing constructed of concentric tubular walls forming spaced chambers therebetween, bead means comprising at least two different covalently bound antigen beads positioned in at least one of said chambers, control bead means without antigen located in another of said chambers; and bead means comprising at least two different covalently bound primary antibodies positioned in at least another chamber and top and bottom cover means on each end of said tubular container.

10. An apparatus as claimed in claim 9 wherein "O" ring means are mounted to the outside of said tubular housing.

11. An apparatus as claimed in claim 10 wherein said "O" ring means comprises a sleeve, said specimen collection unit defining at least four concentric separate bead containing chambers.

12. A container apparatus for collecting a plularity of predetermined markers from biological fluids comprising a cylindrical housing with end means allowing fluid flow therethrough, means dividing said housing into at least four separated isolated chambers, each chamber containing a plurality of beads provided with immobilized ligand means, one of said chambers holding ligand means comprising antigen A and/or antigen B beads and one of said chambers holding control beads, one of said chambers holding ligand means comprising primary anti-A antibody beads and/or anti-B antibody beads and a membrane positioned on one end of said housing with immobilized secondary antibodies affixed thereto.

13. An apparatus for collecting multiple markers from biological fluids comprising a housing removably mounted to a pump means, a biological marker collection means mounted in said housing, said biological marker collection means comprising a plurality of stackable chamber assemblies mounted in said housing to form a plurality of distinct separated chambers, each chamber assembly comprising a porous support member defining a throughgoing aperture, a hollow conduit member mounted to said support member in alignment with said support member aperture to allow fluid flow therethrough, said chamber assemblies when mounted in said housing forming a plurality of distinct separated chambers which separate biological fluid within said housing while allowing biological fluid to flow therethrough, ligand means contained in at least two chambers formed by said chamber assemblies, said ligand means being specifically biologically configured to capture different ligand markers from biological fluid transported through said chambers by said pump means.

14. An apparatus for collecting multiple markers from biological fluids as claimed in claim 13 where said conduit members are cylindrical and are axially aligned with the aperture defined by said porous support member.

15. An apparatus for collecting multiple markers from biological fluids comprising a cylindrical housing open at both ends, said housing being adapted to be removably mounted to a pump means, a specimen collection means mounted in said housing, said specimen collection means comprising a plurality of stackable chamber assemblies removably mounted and concentrically positioned in said housing, each chamber assembly comprising a planar surfaced porous support member defining a throughgoing aperture, a hollow cylindrical conduit member mounted to said support member and extending therefrom, said conduit member being axially aligned with said support member aperture to allow fluid flow therethrough, and a porous cover member mounted to said housing and engaging the distal concentric positioned ends of said conduit members of said chamber assemblies, a circular membrane positioned on the outer surface of the outermost chamber assembly support member, said membrane being provided with an immobilized secondary antibody on its surface, said chamber assemblies when mounted to said housing forming a plurality of concentric separated chambers within said housing, ligand means contained in at least two chambers formed by said chamber assemblies, said ligand means being specifically biologically configured to capture different ligand markers from biological fluid which is transported through said housing by said pump means.

16. An apparatus for collecting multiple markers from biological fluids as claimed in claim 15 where said membrane ranges between 0.45 and 5.0 microns in thickness.

17. An apparatus for collecting multiple markers from biological fluids as claimed in claim 15 where said ligand means in at least two chambers comprise beads which are bound to predetermined various different antigen which constitute biological markers.

18. An apparatus for collecting multiple markers from biological fluids as claimed in claim 15 where said ligand means in at least two chambers comprise beads which are bound to predetermined various different antibodies which constitute biological markers.

19. An apparatus for collecting multiple markers from biological fluids as claimed in claim 15 where said ligand means at least two chambers comprise beads which are bound to predetermined various different antigens and antibodies which constitute biological markers.

20. An apparatus for collecting multiple markers from biological fluids as claimed in claim 15 where said ligand means in one chamber comprises beads which are unbound which acts as a control.

* * * * *